US007029918B2

(12) United States Patent
Li et al.

(10) Patent No.: US 7,029,918 B2
(45) Date of Patent: Apr. 18, 2006

(54) WATER-SOLUBLE DERIVATIVES OF LIPOPHILIC DRUGS

(75) Inventors: Min Li, Ringoes, NJ (US); Robert S. Wu, West Orange, NJ (US); Jane S. C. Tsai, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 625 days.

(21) Appl. No.: 10/057,762

(22) Filed: Jan. 25, 2002

(65) Prior Publication Data

US 2003/0153096 A1    Aug. 14, 2003

(51) Int. Cl.
 G01N 33/548    (2006.01)
 G01N 30/90    (2006.01)
 C07D 243/24    (2006.01)
(52) U.S. Cl. .......................... 436/8; 436/161; 436/530; 436/815; 540/507; 540/510
(58) Field of Classification Search ................ 540/507, 540/510; 436/815, 161, 8, 530
 See application file for complete search history.

(56) References Cited

U.S. PATENT DOCUMENTS

| | | | | |
|---|---|---|---|---|
| 3,567,710 | A | | 3/1971 | Fryer et al. .............. 260/239.3 |
| 3,819,602 | A | * | 6/1974 | Fryer et al. ................. 540/487 |
| 4,043,989 | A | | 8/1977 | Schneider et al. .......... 260/112 |
| 4,046,636 | A | | 9/1977 | Ullman et al. ................ 195/63 |
| 4,083,948 | A | | 4/1978 | Davis et al. .................... 424/1 |
| 4,243,654 | A | | 1/1981 | Schneider et al. ............ 424/12 |
| 4,777,169 | A | | 10/1988 | Earley et al. ............... 514/221 |
| 5,144,030 | A | | 9/1992 | Wang et al. .................. 546/89 |
| 5,237,057 | A | | 8/1993 | Buechler et al. ............ 536/119 |
| 5,770,458 | A | | 6/1998 | Klimov et al. .............. 436/518 |
| 5,847,128 | A | | 12/1998 | Martin et al. | |

FOREIGN PATENT DOCUMENTS

| | | |
|---|---|---|
| DE | 19 23 139 A | 11/1969 |
| EP | 0 246 797 B1 | 11/1987 |
| EP | 264797 A2 * | 4/1988 |
| WO | WO 98/26644 A | 6/1998 |
| WO | WO 01/98289 A1 | 12/2001 |

OTHER PUBLICATIONS

R. Fryer et al, HCAPLUS abstract accession No. 1970: 55525 (1970).*
N. Wang et al, MARPAT abstract accession No. 110: 91693 (1988).*
M. Kanehiro et al, MARPAT abstract accession No. 118: 101995 (1992).*
Yoshimura, Hidetoshi et al., "Synthesis and Pharmacological Activity of a Phosphate Ester of Δ⁸ -Tetrahydrocannabinol", *Journal of Medicinal Chemistry*, (1978), vol. 21, No. 10, pp. 1079-1081.

Zoller, Otmar et al., "High-performance liquid chromatographic determination of Δ⁹-tetrahydrocannabinol and the corresponding acid in hemp containing foods with special regard to the fluorescence properties of Δ⁹-tetrahydrocannabinol", *Journal of Chromatography A*, (2000), 872, pp. 101-110.
Andrew Streitwieser, Jr., et al., University of California, Berkeley, *Introduction To Organic Chemistry*, Third Edition (1985), pp. 698-707, 766-769, 776-780.
Jerry March, Professor of Chemistry, Adelphi University, *Advanced Organic Chemistry—Reactions, Mechanisms, And Structure*, Fourth Edition (1992), pp. 410-411, 499-500, 1199-1200.
W.R. Dixon, et al, *Radioimmunoassay Of The Anticonvulsant Agent Clonazepam*, Journal of Pharmaceutical Sciences, vol. 66, No. 2, Feb. 1977,pp. 235-237.
Bernard Peskar, et al., *Quantitative Determination of Diazepam In Blood By Radioimmunoassay*, The Journal of Pharmacology and Experimental Therapeutics, vol. 186, No. 1 (1973), pp. 167-172.
R. Sherman-Gold, et al., Department of Neurobiology and Department of Chemical Immunology, The Weizmann Institute of Science, *Production of a High Affinity Antiserum to Benzodiazepines*, Journal of Immunoassay, 4(2), 135-146 (1983).
G. Galfrë, et al., *Preparation of Monoclonal Antibodies: Strategies and Procedures*, Methods in Enzymology, vol. 73, Immunochemical Techniques, Part B, John J. Langone, et al, Editors, pp. 3-46 (1981).
Frank L. Adler, et al., *Detection of Morphine by Hemagglutination-Inhibition*, The Journal of Immunology (1971), pp. 1684-1685.
Beier, Ross C. et al. "An antigen based on molecular modeling resulted in the development of a monoclonal antibody-based immunoassay for the coccidiostat nicarbazin" *Analytica Chemica Acta* 2001 444 (1) 61-67.
Edinboro, Leslie E. et al. "Detection of Benzodiazepines And Tribenzazolams By TRIAGE: Confirmation By Solid-Phase Extraction Utilizing SPEC 3ML MP3 Microcolumns And GC-MS" *Journal Of Analytical Toxicology* 1994 18(6), pp. 312-316—Abstract Only.
Partial International Search Report for corresponding Patent Cooperation Treaty application No. PCT/EP03/00655, 3 pages.

* cited by examiner

*Primary Examiner*—Mary E. Ceperley
(74) *Attorney, Agent, or Firm*—Roche Diagnostics Operations, Inc.; Marilyn L. Amick (57) ABSTRACT

A water-soluble reference standard is useful for immunoassays of a lipophilic drugs. The reference standard is a compound of formula (I):

$$G\text{-}(L)_n\text{---}Y; \qquad (I)$$

where G is a lipophilic drug; L is a linker which is an alkyl group or heteroalkyl group containing from 1 to 20 carbon atoms; n is 0 or 1; and Y is a water-solubilizing group such as —$SO_3^-$, —NR—$SO_3^-$, —P(=O)(OH)($O^-$), or —O—P(=O)(OH)($O^-$); where R is H or an alkyl group of 1 to 10 carbon atoms.

3 Claims, 4 Drawing Sheets

WATER-SOLUBLE DERIVATIVES OF LIPOPHILIC DRUGS

BACKGROUND

There is a widespread need for the rapid and accurate detection of the presence of drugs in organisms, including humans. Some drugs may have an optimum window of concentration, within which they have maximum therapeutic effect with minimal side effects. Some drugs may have a threshold concentration above which their long term use can be harmful to the health of the patient. Still other drugs are illegal or are otherwise forbidden or restricted by regulating agencies. Measurement of the presence or amount of a drug in a subject can be accomplished by the analysis of bodily fluids.

Often, the drug of interest is present in a low concentration, making it difficult to obtain an accurate analysis. For example, drugs are often extensively metabolized in an organism, resulting in low concentrations of the drug in urine and plasma samples, and only trace amounts of drugs in saliva samples.

Drugs and/or their metabolites can be detected accurately through Gas Chromatography (GC) and High Pressure Liquid Chromatography (HPLC); however, these methods are expensive and time consuming. Thus, immunoassays for the analysis of drugs in urine and plasma are widely used. Immunoassays can rapidly detect the parent drug compound along with other structurally related drugs, including their metabolites. In general, immunoassays measure the binding between an analyte, such as a drug or drug metabolite, and an antibody for the analyte. These measurements may be done directly, by the detection of the analyte-antibody complex; or they may be done indirectly, by measuring the change in binding of the antibody and an analyte derivative, where the change is due to the presence of the analyte. Immunoassays typically involve the analysis of liquid samples. The liquid may be a free-flowing liquid in a container, or it may be impregnated within a porous or discontinuous solid phase.

Chromatographic immunoassays, which incorporate the use of a porous matrix material into conventional immunoassay techniques, are described, for example, in U.S. Pat. No. 5,770,458, which is incorporated by reference herein. In this format, a complexing reagent is bound to a region of a porous matrix material such as a fibrous or porous membrane. The complexing reagent is either the antibody to the analyte of interest or a derivative of the analyte that has been labeled to allow it to be detected. The liquid sample containing the analyte is loaded onto the matrix material in a region away from the bound complexing reagent and is allowed to migrate through the porous carrier to the region containing the bound complexing reagent. A second complexing reagent may be added to this fluid flow due to its presence within or adjacent to the matrix material or due to addition by the user. The second complexing reagent may also be an antibody to the analyte or a labeled analyte derivative. The measurement of the presence and/or concentration of the analyte can thus be based on detection of complexation between the analyte and two different antibodies (sandwich), the complexation between the analyte and one antibody (direct), or the change in expected complexation between an antibody and a labeled derivative of the analyte (competitive).

The detection of drugs by immunoassays, including chromatographic immunoassays, requires a drug standard. A solution having a known concentration of the drug standard in a buffer formulation is prepared and stored. This concentration and the measured response of the assay to the standard are used to calculate the amount of drug in the test sample. This calibration may be performed before, during, or after the analysis of the sample. For a chromatographic immunoassays, which are typically configured as single-use strips, the calibration may be performed on a representative sampling of the strips as part of the manufacturing process. The standard solution of a predetermined amount of a drug can also be used as Quality Control material.

Drugs which are not readily soluble in water, referred to as hydrophobic drugs or lipophilic drugs, are often difficult to measure by chromatographic immunoassay, since a constant amount of fully soluble drug standard may be difficult to maintain. This solubility behavior has an adverse effect on the determination of analytes in immunoassays and is particularly troublesome in immunochromatographic detection, where the standard solution comes into contact with surfaces such as absorbent pads and porous matrix material. The compound may not stay in a homogeneous state, and an accurate concentration of the standard cannot be consistently maintained. Consequently, the consistency and reproducibility of the drug determination is compromised.

It is thus desirable to provide standards for lipophilic drugs that are useful in immunoassays. It is desirable that these standards are water-soluble. It is also desirable that these standards have adequate mobility under chromatographic immunoassay conditions, and that they are stable in water, specifically in a physiological environment. Such standards ideally will interact specifically with the antibodies that are used in the assays.

SUMMARY

In one aspect of the invention, there is a water-soluble reference standard for an immunoassay of a lipophilic drug, of formula (I):

G is a lipophilic drug; L is a linker selected from the group consisting of alkyl and heteroalkyl containing from 1 to 20 carbon atoms; n is 0 or 1; and Y is a water-solubilizing group selected from the group consisting of $-SO_3^-$, $-NR-SO_3^-$, $-P(=O)(OH)(O^-)$, or $-O-P(=O)(OH)(O^-)$. R is selected from the group consisting of H and an alkyl group comprising 1 to 10 carbon atoms.

In another aspect of the invention, there is a water-soluble reference standard for an immunoassay of benzodiazepines, of formula (II):

$X^1$, $X^2$, $X^3$ and $X^4$ are independently selected from the group consisting of hydrogen, F, Cl, Br, nitro, amino, and alkylamido; E is selected from the group consisting of —H, alkyl, —OH, —COOH, and —COOR', where R' is an alkyl group containing from 1 to 10 carbon atoms; A is an aryl group; L is a linker group selected from the group consisting of alkyl and heteroalkyl containing from 1–20 carbon atoms; n is 0 or 1; and Y is selected from the group consisting of —SO$_3^-$, —NR'—SO$_3^-$, —P(=O)(OH)(O$^-$), or —O—P(=O)(OH)(O$^-$). R' is select from the group consisting of H and an alkyl group comprising 1 to 10 carbon atoms.

The compound has a solubility of at least 100 micrograms per milliliter in water at 25° C.

In yet another aspect of the invention, there is a water-soluble reference standard for an immunoassay of THC, of formula (V):

(V)

L is a selected from the group consisting of alkyl and heteroalkyl containing from 1 to 20 carbon atoms; n is 0 or 1; and Y is selected from the group consisting of —SO$_3^-$, —NR'—SO$_3^-$, —P(=O)(OH)(O$^-$), or —O—P(=O)(OH)(O$^-$). selected from the group consisting of H and an alkyl group comprising 1 to 10 carbon atoms. The compound has a solubility of at least 100 micrograms per milliliter in water at 25° C.

In yet another aspect of the invention, there is a method of forming a water-soluble reference standard for immunoassay of a lipophilic drug, comprising functionalizing a lipophilic drug with a water-solubilizing group selected from the group consisting of —SO$_3^-$, —NR'—SO$_3^-$, —P(=O)(OH)(O$^-$), or —O—P(=O)(OH)(O$^-$).

In yet another aspect of the invention, there is a method of forming a water soluble reference standard for an immunoassay of THC, comprising reacting THC-9-carboxylic acid with DPPA and sodium hydroxide to form THC-9-amine; and treating THC-9-amine with chlorosulfonic acid.

In yet another aspect of the invention, there is a method of forming a water soluble reference standard for an immunoassay of THC, comprising treating THC-9-carboxylic acid with DCC and NHS to form an ester; treating the ester with ammonium hydroxide to form THC-9-amide; reducing the THC-9-amide with lithium aluminum hydride to form THC-9-amine; and reacting the THC-9-amine with chlorosulfonic acid.

In yet another aspect of the invention, there is a method of forming water soluble reference standard for an immunoassay of benzodiazepines, comprising treating didesethylflurazepam with chlorosulfonic acid.

DETAILED DESCRIPTION

The present invention relates to compounds that are water-soluble derivatives of lipophilic drugs. Water-soluble drug derivatives are made by modifying the drug to have a water-solubilizing group attached. These compounds are intended to have increased aqueous solubility and improved stability under immunoassay conditions relative to the original lipophilic drugs. The present invention also relates to the preparation of water-soluble drug derivative compounds and to their use in immunoassays, including chromatographic immunoassays.

The present invention also relates to immunoassays in which water-soluble drug derivatives serve as reference standards for the detection and quantification of the parent lipophilic drug compounds in body fluids such as blood, saliva, and urine. The water-soluble reference standards of the present invention are particularly useful in chromatographic immunoassays. In addition to a reference standard, such as the water-soluble drug derivatives, the chromatographic immunoassay includes an antibody for the analyte, and a labeled derivative of the analyte.

A derivative of a substance, such as a drug, refers to a species having a chemical structure that is similar to the substance, yet containing a chemical group not present in the substance and/or deficient of a chemical group that is present in the substance. The substance to which the derivative is compared is known as the "parent" substance, for example a parent drug or parent compound. A derivative may be made by modification of the parent compound or by synthesis from other starting materials that are not similar to the parent.

Analyte refers to the substance, or group of substances, whose presence or amount thereof in a liquid medium is to be determined including, but not limited to, any drug or drug derivative, hormone, protein antigen, oligonucleotide, hapten, or hapten-carrier complex.

Analyte analog refers to any substance, or group of substances, which behaves in a similar manner to the analyte, or in a manner conducive to achieving a desired assay result with respect to binding affinity and/or specificity of the antibody for the analyte including, but not limited to, derivatives, metabolites, and isomers thereof.

Antibody means a specific binding partner of the analyte and is meant to include any substance, or group of substances, which has a specific binding affinity for the analyte to the exclusion of other substances. The term includes polyclonal antibodies, monoclonal antibodies and antibody fragments.

Haptens are substances, typically of low molecular weight, which are not capable of stimulating antibody formation, but which do react with antibodies. The latter are formed by coupling the hapten to a high molecular weight carrier and injecting this coupled product into humans or animals. Examples of haptens include therapeutic drugs such as digoxin and theophylline; drugs of abuse such as morphine, lysergic acid diethylamide (LSD), and $\Delta^9$-tetrahydrocannabinol (THC); antibiotics such as aminoglycosides and vancomycin; hormones such as estrogen and progesterone; vitamins such as vitamin B12 and folic acid; thyroxin; histamine; serotonin; adrenaline and others.

A carrier refers to an immunogenic substance, commonly a protein, that can join with a hapten, thereby enabling the hapten to stimulate an immune response. Carrier substances include proteins, glycoproteins, complex polysaccharides and nucleic acids that are recognized as foreign and thereby elicit an immunologic response from the host.

The terms immunogen and immunogenic refer to substances capable of producing or generating an immune response in an organism.

A peptide is any compound formed by the linkage of two or more amino acids by amide (peptide) bonds, usually a polymer of α-amino acids in which the α-amino group of each amino acid residue (except the NH$_2$-terminal) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

"Alkyl" refers to a substituted or unsubstituted, straight, branched or cyclic hydrocarbon chain. "Heteroalkyl" refers to an alkyl group containing at least one heteroatom (nitrogen, oxygen, sulfur, or phosphorus). Examples of heteroalkyl groups include ethers, esters, amines, amides, thioethers, ureas, thioureas, carbonates, and carbamates.

"Aryl" refers to any monovalent aromatic carbocyclic group of 5 to 10 carbon atoms. The aromatic group can be polycyclic (i.e. naphthyl), can be substituted, and may include at least one heteroatom. Examples of aryl groups include phenyl, naphthyl, furyl, thienyl, pyridyl, nicotinyl, isonicotinyl, indolyl, quinolinyl, and isoquinolinyl.

Any sample that is suspected of containing the analyte can be analyzed by the method of the present invention. The sample is typically an aqueous solution such as a body fluid from a host, for example, urine, whole blood, plasma, serum, oral fluid, semen, stool, sputum, cerebral spinal fluid, tears, mucus or the like, but preferably is urine, oral fluid, plasma or serum. The sample can be pretreated if desired and can be prepared in any convenient medium that does not interfere with the assay. An aqueous medium is preferred.

Calibration material means any standard or reference material containing a known amount of the analyte to be measured. The sample suspected of containing the analyte and the calibration material are assayed under similar conditions. Analyte concentration is then calculated by comparing the results obtained for the unknown specimen with results obtained for the standard.

The water-soluble reference standards of the present invention are derivatives of drugs, particularly of lipophilic drugs. Generally, the term "lipophilic" means having an octanol/water partition coefficient which is sensitive to pH. For example, a lipophilic drug will have an octanol/water partition coefficient which is higher at a basic pH (pH from 8.5 to 14) than at a neutral pH (pH from 6.5 to 8.5). The term "lipophilic" can also mean having a water solubility less than 100 micrograms per milliliter (μg/mL) of water at 25° C. at neutral pH. Examples of the drugs that may be modified to contain a water-solubilizing group include, but are not limited to, benzodiazepines; cannabinoids, such as THC; opiates, such as heroin, morphine and codeine; cocaine; propoxyphene; phencyclidines, such as PCP; methaqualone; barbiturates; LSD; amphetamines; tricyclic antidepressants; and methadone. Derivatives of lipophilic drugs which are also lipophilic may also be modified to contain a water-solubilizing group.

The water-soluble reference standards of the present invention are compounds of formula (I):

$$G\text{-}(L)_n\text{—}Y \qquad (I),$$

where G is the lipophilic drug or lipophilic drug derivative; L is an alkyl or alkyl ether group containing from 1 to 20 carbon atoms; n is 0 or 1; and Y is a solubilizing group which is sulfamate (—NR—SO$_3^-$), sulfonate (—SO$_3^-$), phosphate (—O—PO$_3^-$), or phosphonate (—PO$_3^-$), where R is H, or an alkyl group containing from 1 to 10 carbon atoms. The solubilizing group Y necessarily includes environment-dependent forms of these groups, including protonated forms (i.e. —NR—SO$_3$H; —SO$_3$H; —O—PO$_3$H; —PO$_3$H) and salts of the groups with appropriate cations, such as sodium, potassium, magnesium, calcium, and ammonium. Preferably, the water-solubilizing group is a sulfamate or a sulfonate. More preferably, the water-solubilizing group is a sulfamate.

The water-soluble reference standards of the present invention may or may not contain a linking moiety (-L-) between the drug (G-) and the water-solubilizing group (—Y). Linkers are well known in the art and are used to provide a spacer between a compound and the solubilizing group. Selection and preparation of an appropriate linking group is described, for example, in U.S. Pat. Nos. 5,144,030 and 5,237,057, which are incorporated herein by reference. The linker may be added to the drug before functionalization with a water-solubilizing group, or the linker may be formed during the functionalization process.

Functionalization of lipophilic drugs with a water-solubilizing group can be accomplished by a variety of synthetic methods. For example, amine groups (—NH$_2$) are readily converted to the corresponding sulfamate (Y=—NR—SO$_3^-$) derivative by treatment with a functionalizing reagent such as chlorosulfonic acid. The amines may be present on the drug itself or may be present on a linker. Amines may be derived from a number of different starting materials by well-known synthetic methods, such as alkylation of ammonia with an alkyl halide and reduction of nitro, nitrile or amide compounds. The Gabriel synthesis is especially useful in the preparation of primary amines via the reaction of an alkyl halide with phthalimide in the presence of base followed by hydrolysis of the alkyl phthalimide intermediate. The conversion of carboxylic acids to a primary amine with the loss of the carboxyl carbon, known as the Schmidt rearrangement, is achieved by treatment of the acid with sodium azide then NaOH. Aldehydes may be converted to amines by treatment with ammonia or an amine followed by hydrogenation, known as reductive amination. Thus, a variety of different groups are readily converted to amines which may be converted to the sulfamates as described above. (See, for example Streitwieser, Jr. et al. *Introduction to Organic Chemistry*, Macmillan, 1985, p.698–707; see also March, *Advanced Organic Chemistry*, John Wiley, 1992, p. 499–500.) Aryl sulfonates are commonly prepared by the electrophilic sulfonation of aromatic compounds using fuming sulfuric acid as the functionalizing reagent, while the alkyl sulfonates may be prepared by the oxidation of thiols with nitric acid or barium permanganate as the functionalizing reagent. The sodium salts of (x-hydroxysulfonic acids may be prepared by the addition of a functionalizing reagent such as sodium bisulfate to a carbonyl compound. Epoxides also may be converted to a-hydroxysulfonic acids by treatment with a functionalizing reagent such as sulfite ion. (See, for example Streitwieser, Jr. et al. *Introduction to Organic Chemistry*, Macmillan, 1985, p.766–769; see also March, *Advanced Organic Chemistry*, John Wiley, 1992, p. 410–411 and 1199–1200.)

Phosphate derivatives (Y=—O—PO$_3^-$) are available via the esterification of phosphoric acid or the hydrolysis of a phosphate triester. The phosphonate deriviatives (Y=—PO$_3^-$) may be prepared from the hydrolysis of phosphonate esters, which are in turn prepared by the Arbuzov-Michaelis reaction. (See, for example Streitwieser, Jr. et al. *Introduction to Organic Chemistry*, Macmillan, 1985, p.776–780.)

For example, a derivative of tetrahydrocannabinol (THC), the primary psychoactive constituent in marajuana, can be readily prepared from commercially available Δ$^8$- or Δ$^9$-THC-9-carboxylic acid (SIGMA, Milwaukee, Wis.), as illustrated in the following reaction scheme.

Conversion of the acid to an amine (THC-9-amine) is achieved by the Curtius rearrangement using diphenyl phosphorous azide (DPPA) followed by sodium hydroxide (NaOH) hydrolysis of the acyl azide intermediate. The resultant amine is treated with chlorosulfonic acid (ClSO₃H) and triethylamine (Et₃N) to yield the water soluble THC-9-sulfamate derivative. This particular derviative does not contain a linking group between the water solubilizing group and the hydrophobic drug.

An example of a method of converting THC-9-carboxylic acid to a water soluble derivative containing a linker, in this case —CH₂—, is illustrated in the following reaction scheme.

The acid is treated with dicyclohexylcarbodiimide (DCC) and N-hydroxysuccinimde (NHS) to form an activated ester, followed by treatment with ammonium hydroxide (NH₄OH). The resultant amide (THC-9-amide) is then reduced to the corresponding amine (THC-9-amine) with lithium aluminum hydride (LAH), and the amine is then treated with chlorosulfonic acid to yield the water-soluble sulfamate derivative (THC-9-methylsulfamate).

Figure 1:
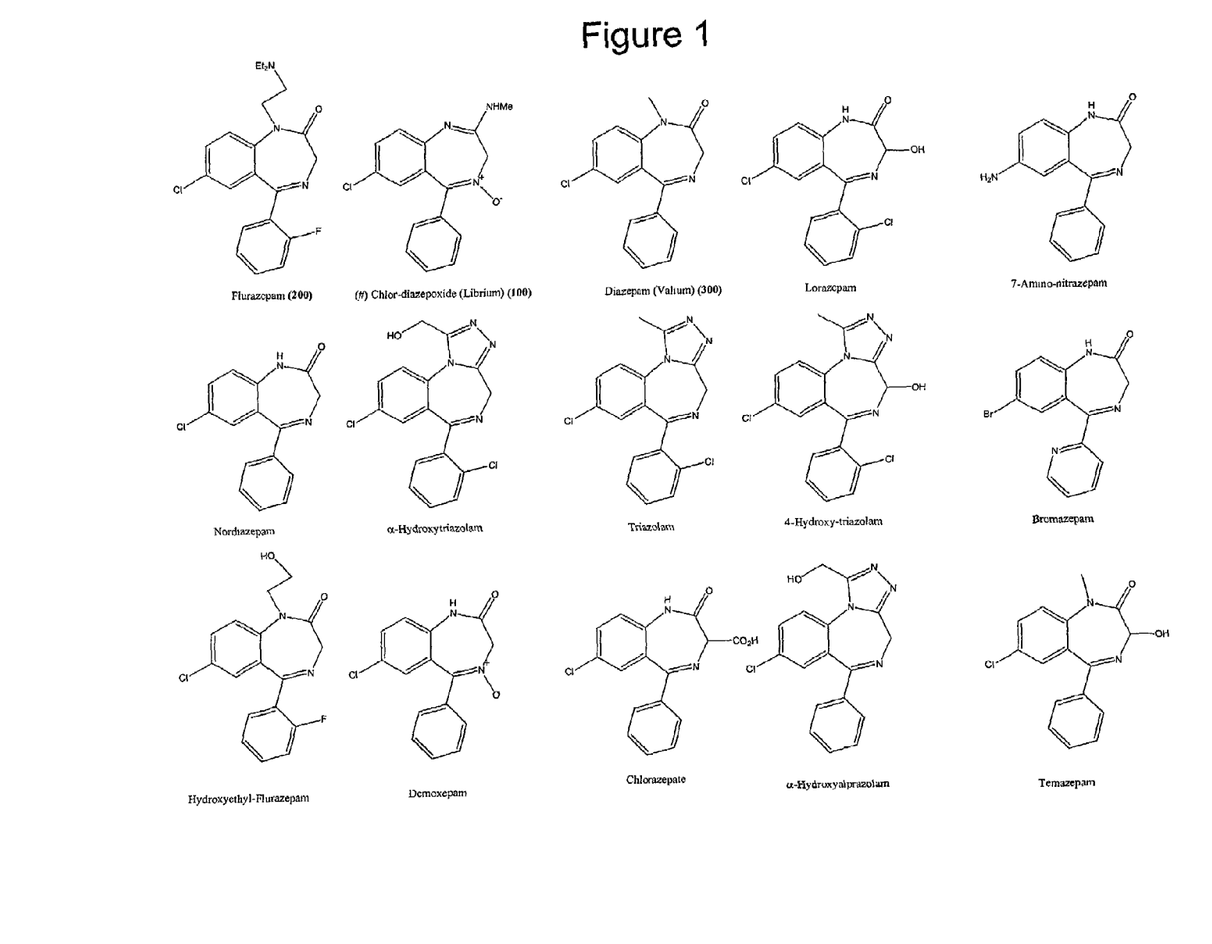
FIG. 1 is a partial list of structures of benzodiazepines.
Figure 2:
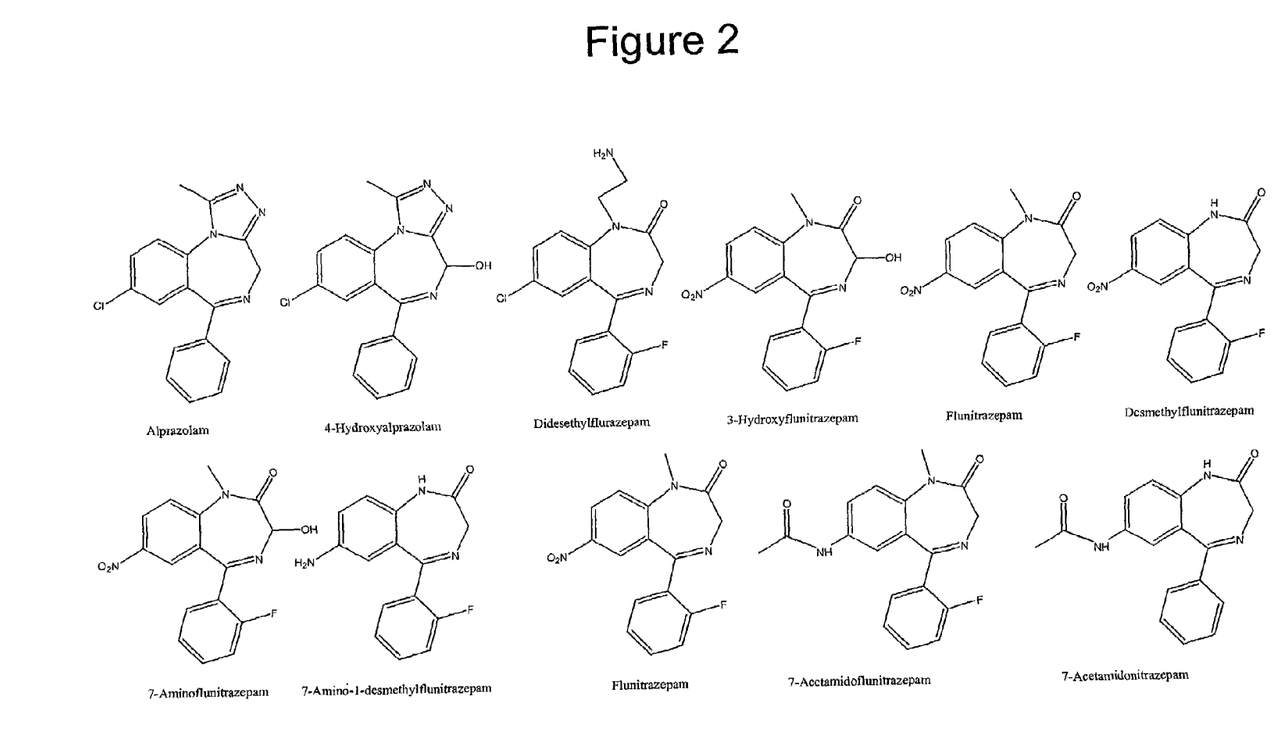
FIG. 2 is a partial list of structures of benzodiazepines.

Another example of a family of lipophilic drugs that can be modified to contain a water-solubilizing group is the benzodiazepines. The benzodiazepines belong to a class of CNS depressant drugs known as sedatives and muscle relaxants. Examples of commonly prescribed benzodiazepines are shown in FIGS. 1 and 2. The serendipitous discovery of the benzodiazepine Librium (100) has led to the development of a variety of analogs, including Flurazepam (200) and Valium (300). These compounds have been extensively prescribed to treat a variety of psychological and physiological disorders including anxiety, depression, insomnia, muscle spasm, headaches, and dyspareunia. Increased dosages of benzodiazepines alone or in combination with other drugs can lead to dependence and may lead to harmful overdoses. Chronic use of benzodiazepines can also cause physical dependence, with withdrawal symptoms including irritability, muscle tension, and, in more severe cases, hallucinations and seizures.

Although it is important to monitor the presence and/or concentration of benzodiazepines and their metabolites in an organism, the compounds typically used as standards for benzodiazepine immunoassays provide mixed results. Conventional compounds used as benzodiazepine standards are Nordiazepam and Oxazepam.

Both Nordiazepam and Oxazepam are lipophilic when in the free base form and have limited solubility in the aqueous buffers used for immunoassays. The free base forms of these compounds are typically solubilized by a small amount of organic solvent such as DMSO or methanol followed by the addition of an appropriate buffer, which decreases the accuracy of the correlation of the standard with the sample. The solubility problems are especially pronounced under solid phase immunoassay conditions where these lipophilic standards can non-specifically adsorb to assay media such as the sample receiving pad the stationary phase. The hydrochloride salts of these compounds are soluble in water and may be used instead of the free base to prepare the standard buffer solution. However, due to the pH sensitivity of their solubility, the use of hydrochloride salts is limited to neutral or acidic conditions (pH≦7). As the pH increases, the free base is generated, and the solubility is reduced. Although

Oxazepam has a slightly higher solubility than Nordiazepam, Oxazepam is unstable in solution, especially at room temperature and above.

The compounds of the present invention include water-soluble benzodiazepine derivatives. Preferably, the water-soluble benzodiazepine derivatives are compounds of formula (II):

where $X^1$, $X^2$, $X^3$ and $X^4$ are independently selected from the group consisting of hydrogen, F, Cl, Br, nitro, amino, or alkylamido; -L- is an alkyl or heteroalkyl group containing from 1–20 carbon atoms; -E is —H, alkyl, —OH, —COOH, or —COOR', where R' is an alkyl group containing from 1 to 10 carbon atoms; A is an aryl group; and Y is the water-solubilizing moiety as described above for formula (I). Preferably, -L- is —CH$_2$CH$_2$—. Preferably —Y is —NHSO$_3$— or —NHSO$_3$H. Preferably, A is selected from the group consisting of phenyl, pyridyl, nictotinyl, isonicotinyl, and substituted derivatives thereof. More preferably $X^1$, $X^2$ and $X^4$ are hydrogen, $X^3$ is Cl; A is 2-fluorophenyl; L is —CH$_2$CH$_2$—; E is H; and Y is NHSO$_3$—.

A preferred water-soluble derivative (2) can be prepared from a benzodiazepine parent didesethylflurazepam (1) according to the following scheme.

The water-soluble reference standards of the present invention have aqueous solubilities, which are greatly increased relative to their corresponding parent compounds. Preferably, the aqueous solubility of a water-soluble drug derivative of the present invention is at least 100 μg/mL at 25° C. More preferably, the aqueous solubility of a water-soluble drug derivative of the present invention is at least 500 μg/mL at 25° C. Even more preferably, the aqueous solubility of a water-soluble drug derivative of the present invention is at least 1 milligram per milliliter (mg/mL) at 25° C.

Water-solubility of the reference standards facilitates their use in the aqueous media of immunoassays. The aqueous solubility also minimizes or eliminates the tendency of the reference standard to non-specifically adsorb to the surfaces encountered in a chromatographic immunoassay. For example, it is believed that water-soluble benzodiazepine reference standard 2 has an aqueous solubility of more than 2 mg/mL, compared to lipophilic benzodiazepine drugs Fluazepam and Diazepam, which have only slight solubility in water. The conventional benzodiazepine standards Oxazepam and Nordiazepam are practically insoluble in water.

The water-soluble reference standards of the present invention are also more stable in aqueous solutions at ambient temperature or higher. Stability is conveniently measured by monitoring the decrease in an initial concentration of the compound in a solution by gas chromatography/mass spectrometry (GC/MS), as described in Example 3 below. The stability of the water-soluble derivatives provides for increased storage times (shelf life) relative to conventional standards, and also permits immunoassays to be performed under a wider variety of conditions, such as at temperatures above ambient. Preferably, water-soluble reference standards of the present invention maintain at least 50% of their initial concentration in aqueous solution at 45° C. for a period of two weeks. More preferably, water-soluble reference standards of the present invention maintain at least 75% of their initial concentration in aqueous solution at 45° C. for a period of two weeks. Even more preferably, water-soluble reference standards of the present invention maintain at least 90% of their initial concentration in aqueous solution at 45° C. for a period of two weeks. Even more preferably, water-soluble reference standards of the present invention maintain at least 93% of their initial concentration in aqueous solution at 45° C. for a period of two weeks.

For instance referring to Example 3, when stored in urine solutions for two weeks, the concentration of water-soluble benzodiazepine reference standard 2 does not change significantly, even at 55° C. By comparison, the concentration of Oxazepam in urine over a two week period does not change significantly when maintained at 4° C., but is reduced by 88% at 45° C. and by 100% at 55° C., due to decomposition of the compound. Referring to Example 4, water-soluble benzodiazepine reference standard 2 exhibits no decrease in stability at 45° C. relative to 4° C. for storage periods as long as 3 months.

The stability of the water-soluble reference standards also is typically not as dependent on the pH of the aqueous solution as are the conventional standards. This toleration of pH permits immunoassays to be performed under a wider variety of conditions, such as in acidic, basic, or neutral conditions. Preferably, the water-soluble reference standards of the present invention maintain at least 50% of their initial concentration in aqueous solution at 45° C. for a period of two weeks at a pH from 2 to 13. More preferably, the water-soluble reference standards of the present invention maintain at least 50% of their initial concentration in aqueous solution at 45° C. for a period of two weeks at a pH from 5 to 9. Even more preferably, the water-soluble reference standards of the present invention maintain at least 50% of their initial concentration in aqueous solution at 45° C. for a period of two weeks at a pH from 6 to 8.

For instance, referring again to Example 3, the concentration of water-soluble benzodiazepine reference standard 2 does not change significantly when stored for up to 4 weeks, either at 4° C. or at 45° C., whether the pH is acidic (pH=6.4) or basic (pH=7.4). This stability is observed for concentrations at least between 100 ng/mL and 200 ng/mL.

The water-soluble reference standards are soluble in aqueous environments having basic, neutral, or acidic pH's. This results in an octanol/water partition coefficient for the water-soluble reference standard which is constant within an aqueous pH from 2 to 14. A constant octanol/water partition coefficient is defined as having a value which varies by less than ±5% over the specified pH range. Preferably, the octanol/water partition coefficients of the water-soluble reference standards are constant within a pH from 3 to 12. More preferably, the octanol/water partition coefficients of the water-soluble reference standards are constant within a pH from 5 to 9.

The water-soluble compounds of the present invention are useful as standards in immunoassays. The water-soluble reference standards form complexes with antibodies at a similar level to those formed by the drug or a labeled drug derivative. Thus, the response of an immunoassay to a range of concentrations of a water-soluble reference standard can be used to construct a calibration curve for the immunoassay. In addition to a useful standard compound, a system for immunoassay of a drug also includes an antibody and a labeled derivative of the drug. Preferably, the system is a competitive binding immunoassay and includes both an antibody and a drug derivative conjugated with a carrier.

For chromatographic immunoassays, such as those described in U.S. Pat. No. 5,770,458, the reference standards are used to develop the assay product, to assist in formulation of the product during manufacture, and to insure the reliability of the product by testing selected samples (i.e. quality control). Variables in the ingredients of chromatographic immunoassay strips include, for example, the concentration of antibody or drug derivative on the porous matrix material; the concentration of the corresponding binding partner on any particles used; and the porosity of the matrix material.

Antibodies may be prepared in an antiserum by standard methods, such as those disclosed in *J. Pharm. Sci.* 66, 235 (1977); *Biochem. Pharm. Exp. Therapeutics* 186,167 (1973); J. Imm. 4, 135 (1983); U.S. Pat. Nos. 4,243,654; 4,046,636; 4,777,169; 4,043,989; and 4,083,948. Preparation of polyclonal antibodies using an immunogen may follow any of the conventional techniques known to those skilled in the art. Commonly, a host animal such as a rabbit, goat, mouse, guinea pig, or horse is injected with the immunogen mixture. Further injections are made, with serum being assessed for antibody titer until it is determined that optimal titer has been reached. The host animal is then bled to yield a suitable volume of specific antiserum. Where desirable, purification steps may be taken to remove undesirable material such as nonspecific antibodies before the antiserum is considered suitable for use in the performing assays. Monoclonal antibodies may be obtained by hybridizing mouse lymphocytes, immunized as described above, and myeloma cells using a polyethylene glycol method such as the technique described in *Methods in Enzymology* 73 (Part B), pp3–46, 1981. Conjugates with bovine serum albumin (BSA) are preferred for coating of microtiter plates for use in Elisa. This method has been used to screen the antibodies and is well-known to those skilled in the art. In order to provide an optimum antibody-antigen reaction that can be readily displaced by the analyte containing structurally related drugs, the preferred antibodies are raised by immunizing animals with a conjugate of the drug or drug derivative with a carrier. Preferably, the carrier is a protein.

More preferably, the carrier is Bovine Serum Albumin (BSA) or Bovine Thyroglobulin (BTG). For example, for a given water-soluble benzodiazepine derivative, it is preferred that an immunogen of formula (III) is used.

wherein $X^1$, $X^2$, $X^3$, $X^4$, A, E, and L are as described above; and T is a carrier.

For example, for the specific water-soluble benzodiazepine derivative (2), a preferred immunogen for raising antibodies may be prepared according to the following reaction scheme.

The acid compound (3) may be made by standard methods, such as by reaction of compound 1 with succinic anhydride in the presence of a base such as triethylamine. The acid compound 3 can then be coupled to a variety of carriers, including proteins, to provide a benzodiazepine immunogen. Preferably the acid compound is coupled to BSA or BTG. Other well known methods for the preparation of the protein conjugates may be employed as well.

In addition to antibody, a drug-carrier conjugate may be useful in performing immunoassays. Carriers may be tracers such as enzymes, including β-galactosidase and peroxidase; fluorescent molecules including fluorescein compounds; radioactive elements including $^{125}I$; microparticles; and proteins including BSA and BTG. Carriers may be colored colloidal particles, such as colored latex or metal nanoparticles. Colored latex and gold sol are readily visible to the naked eye when bound in the detection zone of a chromatographic immunoassay, reducing or eliminating the need for additional developing procedures.

For example, for benzodiazepines the preferred conjugate has a structure according to general formula (IV)

(IV)

wherein $X^1$, $X^2$, $X^1$, $X^4$, Z, and A are the same as defined above; Z is a linking group as described for L above; Q is an alkyl group containing from 1–20 carbon atoms; and T is a carrier. Preferably, $X^3$ is Cl; Z is NHCOCH$_2$CH$_2$CH$_2$CO—; and A is phenyl. Preferably T is BSA. A preferred conjugate may be prepared according to the following scheme.

In the absence of lipophilic drug in a sample being analyzed, the drug conjugate can bind to the antibody, and this binding can be measured. When a the lipophilic drug is present in the sample, the drug competes with the drug conjugate for binding to the antibody. Antibody that is bound to the lipophilic drug no longer contributes to the binding measurement. Lipophilic drug content is determined relative to the values obtained for known concentrations of the standard compound (Adler, F. L. *J. Immunol.* 1971, 106(6): 1684–1685. See also Bates, M. *Amer. Acad. Forensic Sci.* 1991, 37(6):1000).

Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumin, or surfactants, particularly non-ionic surfactants, or the like.

The water-soluble drug derivatives may, along with other reagents, be packaged in a kit useful for conveniently performing the assay methods for the determination of an analyte. To enhance the versatility of the subject invention, reagents can be provided in packaged combination, in the same or separate containers, in liquid or lyophilized form so that the ratio of the reagents provides for substantial optimization of the method and assay. The reagents may each be in separate containers, or various reagents can be combined in one or more containers depending on the cross-reactivity and stability of the reagents.

For example, a reference standard kit may contain, in packaged combination, an antibody specific for a particular drug, a complex comprising a ligand of a drug derivative coupled to a labeling moiety, and further comprising one or more water-soluble drug derivatives (reference standard) in a known amount for calibration of the immunoassay. Such a reference standard kit may provide reagents for an assay with enhanced clinical sensitivity for lipophilic drugs and structurally related compounds.

EXAMPLES

The following examples are provided as an illustration and should not be seen as limiting the scope of the invention. Reagents and solvents mentioned in these examples are available generally from SIGMA-ALDRICH (Milwaukee, Wis.) or FISHER (Suwanee, Ga.).

Example 1

Synthesis of 1-(2-Sulfamidoethyl)-2'-fluoro-7-chloro-1, 4-benzodiazepine (2)

To a suspension of 405 mg (1.0 mmol) of 1-(2-aminoethyl)-2'-fluoro-7-chloro-1,4-benzodiazepine dihydrochloride (1, HOFFMANN-LA-ROCHE INC, Nutley, N.J.) in 20 mL of methylene chloride at room temperature was added dropwise a solution of 840 μL (6.0 mmol) of triethylamine in 2 mL of methylene chloride. After the resulting mixture was stirred for 30 min, 140 μL (2.1 mmol) of chlorosulfonic acid was added dropwise. The reaction mixture was allowed to stir for 1 h and then extracted with water (60 mL×4). The organic phase was discarded and all aqueous phases were combined. The pH of the combined aqueous solution was adjusted to 10.5–11 with a 35% NaOH solution and the basic solution was extracted with methylene chloride (65 mL×6). The extracted aqueous solution was evaporated in vacuo to dryness, yielding 426 mg of crude product, which was shown to contain about 12% (wt/wt) of the sulfate salt of triethylamine. To purify the product, 200 mg of the crude material was dissolved in ~14 mL of water and a portion of the resulting solution (2 mL) was injected onto a RAININ preparative HPLC system equipped with a WATERS pre-packed C-18 cartridge column (25×100 mm) (VARIAN, Palo Alto, Calif.). The elution was made isocratically with a mobile phase of 10 mM ammonium acetate/acetonitrile (70/30, v/v) at a flow rate of 7.0 mL/min. UV detection at 308 nm was selected and the fraction eluted at ~8–9 min was collected. The remaining crude solution was purified using the same procedure. After all 7 purification runs were completed, all the fractions collected at ~8–9 min were combined and then evaporated to dryness. The dried powder was dissolved with about 50 mL of water and the mixture centrifuged. The supernatant was then transferred to a 100-mL round bottom flask for lyophilization, yielding 175 mg of white powder. $^1$H-NMR (CDCl$_3$, 200 MHz) δ7.82 (d, 1H, J=9 Hz), 7.51–7.68 (m, 3H), 7.33 (t, d, 1H, J$_1$=7.6 Hz, J$_2$=1.1 Hz), 7.10–7.22 (m, 2H), 4.68 (d, J=10.7 Hz), 4.27 (quintet, 1H, J=7.0 Hz), 4.03 (quintet, 1H, J=7.0 Hz), 3.88 (d, 1H, J=10.7 Hz), 3.25 (t, 2H, J=7.0 Hz).

Example 2

Preparation of Urine Standard Solutions for Immunoassays

Urine standard solutions were prepared using pooled, filtered, normal human urine containing 0.09 percent sodium azide. The urine pool was certified to be drug-free as determined by the GC-MS analysis of a panel of drugs including benzodiazepines. The urine pool was aliquoted for the preparation of the three different sets of urine standards, each containing either water-soluble derivative 2, Oxazepam, or Nordiazepam. The urine pool had a pH value of 7.4 and an aliquot of the pool was adjusted to pH 6.4 to compare the stability of water-soluble derivative 2 in acidic versus neutral urine. Each of the drug stock solutions was added analytically to the assigned aliquot of urine pool. Final drug concentrations in the solutions were determined by GC-MS analyses performed at ELSOHLY LABORATORIES (Oxford, MS).

Example 3

Stability Studies of Urine Standard Solutions

The stability of the above standard solutions were evaluated using three different analytical technologies: (1) GCIMS (Gas Chromatography/Mass Spectrometry) analysis, (2) ABUSCREEN ONLINE Benzodiazepines Immunoassay, and (3) HPLC (High Pressure Liquid Chromatography) analysis.

ABUSCREEN ONLINE reagents and Calibration Pack were obtained from ROCHE DIAGNOSTICS CORPORATION, INC. (Indianapolis, Ind.). ABUSCREEN ONLINE Benzodiazepines assay was run either on a ROCHE MIRA analyzer in a semi-quantitative mode, or using a ROCHE COBAS INTEGRA 700 analyzer in a semi-quantitative mode, according to the I manufacturer's instructions.

The standard solutions were stored at various temperatures, including 4° C., 45° C. and 55° C., and tested at different time intervals. The comparison of heat stress stability of Oxazepam and water-soluble derivative 2 was performed using GC/MS quantification. As shown in Table A, there was a 100% loss of Oxazepam at 55° C., and 88% loss of Oxazepam at 45° C. in two weeks. In contrast, water-soluble derivative 2 was stable at all temperatures, and the respective GC/MS values are all within the acceptable imprecision range for GC/MS analysis (i.e., within ±20% of the starting concentration at Day 0). When the solutions of water-soluble derivative 2 were evaluated again at 5 months, the GC/MS values were 147 ng/mL, 150 ng/mL and 145 ng/mL for 4° C., 45° C. and 55° C., respectively. These values are also within the acceptable imprecision range for GC/MS analysis (i.e., within ±20% of the starting concentration at day zero).

TABLE A

| Temperature | 4° C. | 45° C. | 55° C. |
| --- | --- | --- | --- |
| Oxazepam Day 0 = 196 ng/mL | 196 | 24 | 0 |
| Water-soluble deriv. 2 Day 0 = 171 ng/mL | 191 | 178 | 185 |

The heat stress stability study of the water-soluble derivative 2 was evaluated using ABUSCREEN ONLINE Benzodiazepines assay. As shown in Table B, ONLINE assay was used to evaluate two Nordiazepam standards at 4° C. and four different standard preparations of water-soluble derivative 2 at 4° C. and 45° C. (in neutral and acidic negative urine pools, 2 concentrations for each urinary pH). All four preparations or water-soluble derivative 2 were stable for the evaluated time and temperatures.

TABLE B

| | | 4° C. | | | 45° C. | | |
| --- | --- | --- | --- | --- | --- | --- | --- |
| | pH | Day 0 | Week 2 | Week 4 | Day 0 | Week 2 | Week 4 |
| 2 (ng/mL) | 7.4 | 102 | 92 | 99 | 102 | 95 | 98 |
| 2 (ng/mL) | 7.4 | 188 | 183 | 189 | 188 | 179 | 192 |
| 2 (ng/mL) | 6.4 | 99 | 97 | 106 | 99 | 101 | 109 |
| 2 (ng/mL) | 6.4 | 191 | 191 | 193 | 191 | 200 | 209 |

TABLE B-continued

| | | 4° C. | | | 45° C. | | |
|---|---|---|---|---|---|---|---|
| | pH | Day 0 | Week 2 | Week 4 | Day 0 | Week 2 | Week 4 |
| Nordiazepam (ng/mL) | 7.4 | 139 | 140 | 134 | 139 | N.D. | N.D. |
| Nordiazepam (ng/mL) | 7.4 | 271 | 272 | 252 | 271 | N.D. | N.D. |

Example 4

Stability Study of Water-Soluble Derivative 2 Spiked in Urine Using HPLC

Water-soluble derivative 2 was spiked in certified drug-free human urine 100 ng/mL) and the resulting solution was divided into two portions: one was stored at 4° C. and the other stressed at 45° C. After three months, both solutions were analyzed for the concentration of water-soluble derivative 2 by the following procedure. A volume (between 2.5 to 10 mL) of the urine solutions was passed through an affinity column packed with anti-benzodiazepines antiserum-coated latex beads (0.8 μm). After it was washed with a 50 mM, pH 6.1 MES (4-morpholineethane Sulfamyl) buffer, the column was eluted with methanol. The methanol eluant was then evaporated and the residue reconstituted in 404 μL of MES buffer. An 80 μL aliquot of the reconstituted buffer was injected into an HP 1100 HPLC system equipped with a 4.6×150 mm Hypersil C18 column and a UV-Vis diode-array detector (with scnning detection from 220 to 460 nm) (THERMO HYPERSIL-KESTONE (Bellefonte, Pa.)). The column was eluted with a gradient generated between a 50 mM, pH 6.8 ammonium acetate buffer and acetonitrile (Table C).

TABLE C

| Time | 50 mM NH$_4$OAc (%) | Acetonitrile (%) | Flow (mL/min) |
|---|---|---|---|
| 0 | 100 | 0 | 1.00 |
| 30 | 60 | 40 | 1.00 |
| 40 | 30 | 70 | 1.00 |
| 60 | 100 | 0 | 1.00 |

The water-soluble derivative 2 eluted at approximately 18 min and its area count at 220 nm was used for quantification. The relative stability of the stressed sample was found to be 101% (average of duplicate extraction and HPLC runs that gave 96% and 106%, respectively), which was defined as the area count of the stressed sample at 45° C. divided by that of the sample stored at 4° C.

Example 5

Synthesis of 1-(2-succinateamidoethyl)-2'-fluoro-7-chloro-1,4-benzodiazepine (3)

To a suspension of 810 mg (2.0 mmol) of 1-(2-aminoethyl)-2'-fluoro-7-chloro-1,4-benzodiazepine dihydrochloride (1) and 0.7 mL (5.0 mmol) of triethylamine in 30 mL of methylene chloride at room temperature was added 220 mg (2.2 mmol) of succinic anhydride. The reaction mixture was stirred for 20 h at ambient temperature under argon. The solution was washed with 30 mL of 0.1 N HCl and 3×30 mL of water. Methylene chloride was evaporated to dryness to give an oil. This was passed through a silica gel column using a mixture of methylene chloride/methanol (90/10) as the eluent. The desired product fraction was collected and the organic solvent was evaporated to dryness to give an amorphous beige solid (905 mg). $^1$H-NMR (CDCl$_3$, 200 MHz) compatible with the given structure.

Example 6

Preparation of Benzodiazepine Immunogen (4)

To a solution of 40 mg of benzodiazepine acid 3 in 5 mL of methylene chloride was added 30 mg of N-hydroxy succinimide and 50 mg of EDC. The mixture was stirred for 20 h under argon. The organic layer was washed with 2×10 mL of 0.1 N HCl, 2×10 mL of saturated sodium bicarbonate and 2×10 mL of water. The organic layer was dried in anhydrous sulfate and the solvent was removed under reduced pressure to give an oil. This was dissolved in 5 mL of dry DMSO and put aside for protein coupling described below.

BTG (800 mg) was dissolved in 16 mL of 50 mM potassium phosphate pH 7.5. The solution was cooled in an ice bath and DMSO (16 mL) was added slowly. The ice bath was removed and to this was added dropwise the 5 mL solution of the benzodiazepine active ester prepared as mentioned above. The mixture was stirred for 20 h at ambient temperature and the resulting immunogen was poured into a dialysis bag of a 50 K cut-off. The bag was dialyzed in 1 L solution of DMSO/50 mM potassium phosphate pH 7.5 (6:4), in 1 L solution of DMSO/50 mM potassium phosphate pH 7.5 (3:7). in 1 L solution of DMSO/50 mM potassium phosphate pH 7.5 (15:85), in 1 L solution of DMSO/50 mM potassium phosphate pH 7.5 (5:95) and in 1 L solution of 50 mM potassium phosphate pH 7.5. The immunogen was then filtered through a 0.22 micron filtration cup and its protein content was determined by the COOMASIE BLUE assay (BIORAD, Hercules, Calif.). Aliquots of this immunogen were frozen and ready for use in animal immunization.

Example 7

Preparation of Activated Benzodiazepine Derivative (6)

To a solution of 10.0 g (0.0876 mole) of glutaric anhydride in 50 mL of THF was added 10.0 g (1 mole) of N-hydroxysuccinimide (NHS) and the reaction mixture boiled under reflux for 3.5 h. The resulting solution was concentrated under reduced pressure to an oil. The material was taken up in 50 mL of ethyl acetate and crystallization induced to yield a solid material which was filtered and washed with a little ethyl acetate to yield 15.8 g (79%) of 5-[(2,5-dioxo-1-pyrrolidinyl)oxy]-5-oxo-pentanoic acid. Re-crystallization from ethyl acetate and hexane afforded white needles. M.P.: 81–83° C. MA.

Calc. For C$_9$H$_{11}$NO$_6$: C, 47.17; H, 4.84; N, 6.11. Found: C, 46.99; H, 4.87; N, 6.11.

To a solution of 10.0 g (0.044 mole) of the glutarate mono-NHS ester obtained above, in 20 mL of thionylchloride was heated in 45° C. under a reflux condenser under argon. Volatile material was then removed by direct aspiration of the reaction flask under vacuum through a cold trap (cooled by dry ice-acetone to give 8.5 g, 79% of the glutarate mono-NHS ester mono acid chloride as a white solid, shown by $^1$H-NMR to be of good purity.

3-Aminobenzodiazepine (5, obtained from Hoffmann-La-Roche) (2.95 g, 0.008 mole) and triethylamine (3 mL) were dissolved 150 mL of THF. The solution was cooled in an ice bath and then, added with 2.7 g (0.011 mole) of the glutarate mono-NHS ester mono acid chloride prepared above. This was stirred for 15 min. at ~0° C. and the organic solvent was removed to give pale yellow foam. The material was dissolved in 100 mL of methylene chloride and the organic phase was washed with 50 mL of water, 50 mL of saturated sodium bicarbonate, and again with 50 mL of water. The organic layer was dried over anhydrous magnesium chloride. Evaporation of methylene chloride solvent affords a foam (1.8 g). The foam was recrystallized from methylene chloride and diethyl ether to yield 1.5 g of compound 5 as an off white solid. 1H NMR is compatible with the given structure. The compound is ready for coupling with BSA as described below.

Example 8

Preparation of benzodiazepine-BSA Conjugate (7)

The benzodiazepine-BSA conjugate was prepared in a similar manner as described in Example 6, but treating with BSA rather than BTG. The product was prepared and stored in 100 mM potassium phosphate as 10 mg/mL solution with 0.05% sodium azide as preservative Example 9-Immunochromatographic assay of benzodiazepines using water-soluble derivative 2 as calibrator The immunochromatographic assay was conducted using a nitrocellulose-based test strip as described in detail in U.S. Pat. No. 5,770,458. Mylar backed large pore size nitrocellulose (8–12 micron) was cut into pieces of 15 cm in length and 5 cm in width. A solution of the benzodiazepine-BSA conjugate 7 (about 5 mg/mL) and anti-BSA monoclonal antibody (about 2 mg/mL), both in 50 mM potassium phosphate buffer pH 7.5, were loaded onto IVEK CORP. (North Springfield, Vt.) DIGISPENSE 2000™ system. The solutions were dispensed at the rate 1 μl/cm onto nitrocellulose at a distance of 2 cm and 1 cm, respectively, from the 15 cm side. The nitrocellulose segments were allowed to dry for about 30 min. at 37° C., and then were blocked with polyvinyl alcohol (PVA, m.w. 13,000–23,000) solution in 20 mM TRIS, pH 8, for 30 min. at room temperature. The segments were then rinsed in water and dried.

The same nitrocellulose as described above in this example was used as a separate membrane for microparticles (top membrane). The construction of the two-membrane strip configuration was carried out as described in detail in U.S. Pat. No. 5,770,458. In brief, the top membrane was blocked and washed using the same protocol as the main membrane. The top membrane containing the appropriate amount of microparticles was laminated to the main membrane with ADHESIVE RESEARCH INC. (Glen Rock, Pa.) adhesive mylar and the segment was then cut into 5 mm wide strips. The sample pad and sink pad were placed respectively at the beginning and terminal ends of the strips. Cellulose from BIORAD LABORATORIES (Hercules, Calif.) (gel blotter) was used for both the sample receiving pads and the sink pads. The calibration curve was obtained by adding solutions containing predetermined amounts of drug in urine to the sample receiving pad or by dipping the sample receiving pad of the membrane strip in the solutions. Various predetermined concentrations of water-soluble derivative 2 were used to prepare the standards in urine. The signal strength is determined as follows: 2.5 to 3.0=dark blue, 1.5 to 2.0=medium blue, 1.0=light blue, 0.5=barely perceivable color and 0=colorless. When the strip read colorless, a complete inhibition is achieved and the sample is indicated to contain 200 ng/mL of the drug used to prepare the "standards".

Figure 3:
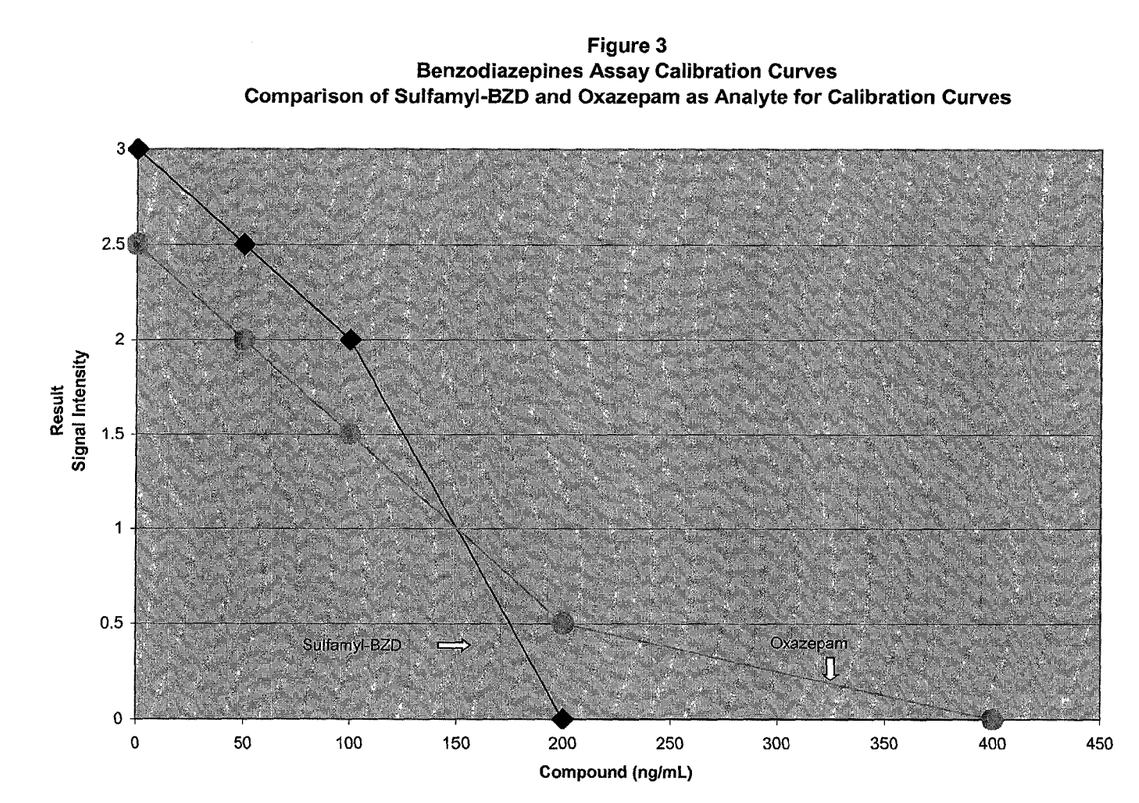
FIG. 3 is a comparison of the benzodiazepine assay calibration curves generated using water-soluble derivative 2 and Oxazepam.
Figure 4:
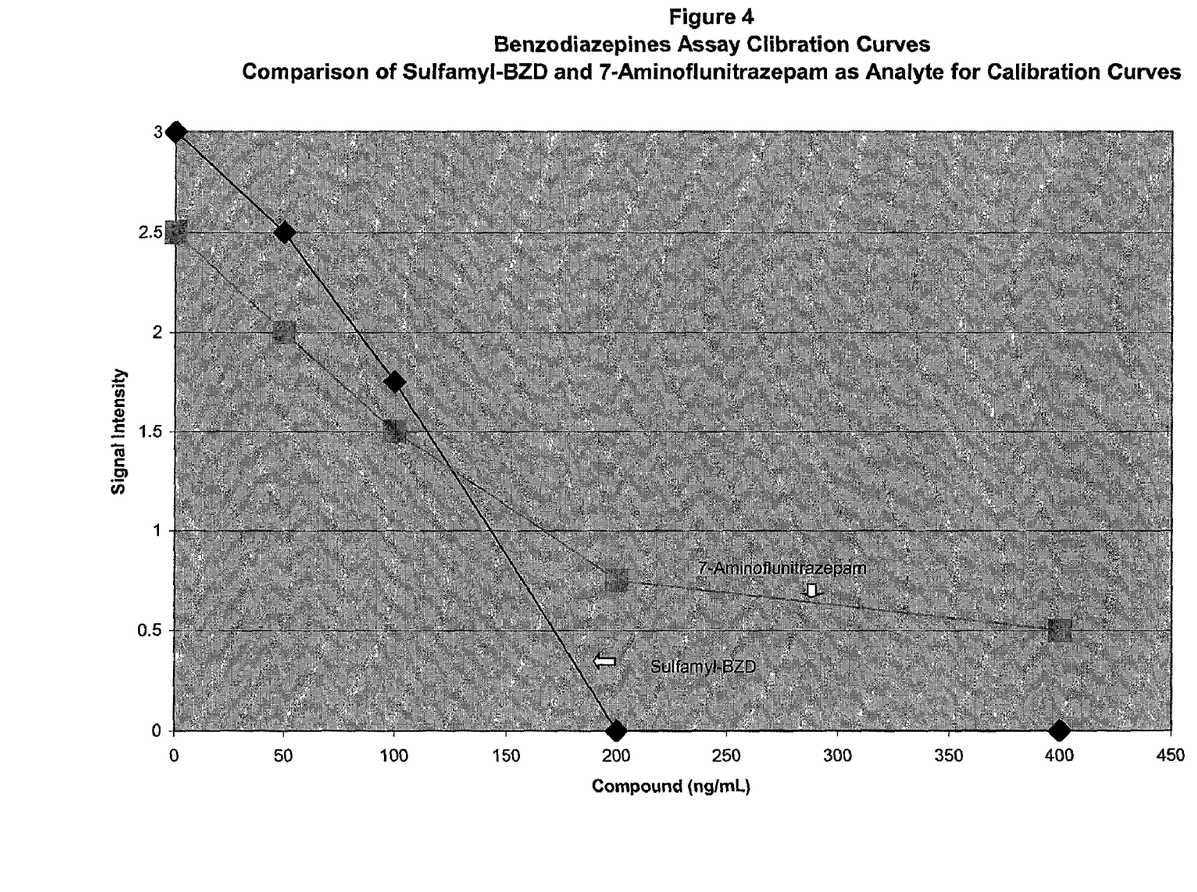
FIG. 4 is a comparison of the benzodiazepine assay calibration curves generated using water-soluble derivative 2 and 7-aminoflunitrazepam.

The comparison of the benzodiazepine assay calibration curves generated using water-soluble derivative 2 and Oxazepam is shown in FIG. 3. The comparison of the benzodiazepines assay calibration curves generated using water-soluble derivative 2 and 7-aminoflunitrazepam is shown in FIG. 4. The calibration curves produced using water-soluble derivative 2 as the calibrator have the largest span and the best near-cutoff differentiation.

Examples of calibration curve reproducibility are shown in Table D.

TABLE D

| Standard Used | Benzodiazepine standard concentration (ng/mL) | | | | |
| --- | --- | --- | --- | --- | --- |
| | 0 | 50 | 100 | 200 | 400 |
| Derivative 2 | 3.00 | 2.50 | 2.00 | 0 | 0 |
| Derivative 2 | 3.00 | 2.75 | 2.00 | 0 | 0 |
| Derivative 2 | 3.00 | 2.50 | 2.00 | 0 | 0 |
| Oxazepam | 2.50 | 2.00 | 1.50 | 0.50 | 0 |
| Oxazepam | 2.50 | 2.00 | 1.00 | 0.50 | 0 |

The cross-reactivity of water-soluble derivative 2 to both Oxazepam and Nordiazepam is approximately 70% as determined by both ONLINE immunoassay and immunochromatographic assay. When the concentration is adjusted appropriately, it can replace Nordiazepam and/or Oxazepam to calibrate the assay without compromising the ability for the assay to detect other benzodiazepine-like compounds.

The above preferred embodiments and examples are given to illustrate the scope and spirit of the present invention. These embodiments are not intended to limit the invention, but will make apparent to those skilled in the art other embodiments and examples within the contemplated scope of the invention. Therefore, the present invention should be limited only by the following claims.

What is claimed is:

1. A water-soluble reference standard of formula (II)

wherein $X^1$, $X^2$, $X^3$ and $X^4$ are independently selected from the group consisting of hydrogen, F, Cl, Br, nitro, amino, and alkylamido;

-L- is —CH$_2$CH$_2$—;

-E is —H, alkyl, —OH, —COOH, or COOR', where R' is an alkyl group containing from 1 to 10 carbon atoms;

A is an aryl group; n is 1; and Y is —NHSO$_3$.

2. The water-soluble reference standard of claim 1, wherein $X^1$, $X^2$, and $X^4$ are hydrogen;

$X^3$, Cl; and

A is 2-fluorophenyl.

3. A reference standard kit, comprising the reference standard of claim 1.

* * * * *